United States Patent [19]

DeVries

[11] Patent Number: 4,582,929
[45] Date of Patent: Apr. 15, 1986

[54] METHOD OF RECOVERING HALIDE VALUES FROM CARBONYLATION REACTION MIXTURES

[75] Inventor: Robert A. DeVries, Midland, Mich.

[73] Assignee: The Dow Chemical Company, Midland, Mich.

[21] Appl. No.: 686,174

[22] Filed: Dec. 24, 1984

[51] Int. Cl.$^4$ ............................................. C07C 51/10
[52] U.S. Cl. ..................... 562/406; 562/497; 562/520; 560/104; 560/206; 560/207; 564/132; 260/544 A
[58] Field of Search ........................ 562/406, 497, 520; 560/104, 206, 207; 260/544 A; 564/132

[56] References Cited

U.S. PATENT DOCUMENTS

| | | | |
|---|---|---|---|
| 3,457,299 | 7/1969 | Closson et al. | 560/206 |
| 3,626,005 | 12/1971 | Scheben et al. | 260/544 A |
| 3,988,358 | 10/1976 | Heck | 260/465 D |
| 3,991,101 | 11/1976 | Knifton | 560/206 |
| 4,094,957 | 6/1978 | Sartori et al. | 423/223 |
| 4,115,530 | 9/1978 | Coenen et al. | 423/488 |
| 4,217,238 | 8/1980 | Sartori et al. | 252/192 |
| 4,230,681 | 10/1980 | Coenen et al. | 423/481 |
| 4,272,502 | 6/1981 | Ziegenbein et al. | 423/488 |
| 4,405,578 | 9/1983 | Sartori et al. | 423/223 |
| 4,424,375 | 1/1984 | El-Chahawi et al. | 562/406 |

FOREIGN PATENT DOCUMENTS

| | | |
|---|---|---|
| 0031200 | 7/1981 | European Pat. Off. . |
| 9027848 | 2/1984 | Japan . |

*Primary Examiner*—Paul J. Killos

[57] ABSTRACT

This invention is a process for the carbonylation of an organic halide to prepare a carbonyl-containing compound, and recovery of halogen values in a useful form which comprises (a) contacting an organic halide with carbon monoxide and an esterifying agent, a primary or secondary amine, or hydrogen gas, in an inert organic solvent in the presence of a water-insoluble tertiary amine or pyridine ring-containing compound, and a catalytic amount of a Group VIII metal catalyst, under conditions such that an organic ester, amide or aldehyde is prepared and the halide generated in the process forms a salt with tertiary amine or pyridine compound wherein the halide is bromine or iodine;

(b) separating the organic ester, amide or aldehyde from the reaction mixture which contains the tertiary amine or pyridine compound-halide salt;

(c) contacting the reaction mixture containing the tertiary amine or pyridine compound-halide salt mixture with a concentrated aqueous solution of an alkali metal base or alkaline earth metal base under conditions such that an aqueous solution of an alkali metal halide or an alkaline earth metal halide and reaction solution containing the tertiary amine or pyridine compound is prepared;

(d) separating the aqueous solution from the reaction mixture; and (e) contacting the aqueous solution containing the alkaline earth metal halide salt or alkali metal halide salt with chlorine under conditions such that an alkali metal chloride salt or alkaline earth metal chloride salt and elemental halide is prepared.

8 Claims, No Drawings

METHOD OF RECOVERING HALIDE VALUES FROM CARBONYLATION REACTION MIXTURES

BACKGROUND OF INVENTION

This invention relates to a process for the carbonylation of an organic halide, wherein the halogen values generated by such process are recovered in a usable form.

Heck, U.S. Pat. No. 3,988,358 (incorporated herein by reference) discloses a process for the preparation of carboxylic acid esters from organic halides, which comprises carbonylation of an organic halide in the presence of a palladium catalyst and a tertiary amine. Heck, U.S. Pat. No. 3,960,932 (incorporated herein by reference), discloses the preparation of aldehydes by reacting organic halides with carbon monoxide and hydrogen in the presence of a basic tertiary amine and a palladium metal catalyst. Heck, U.S. Pat. No. 4,128,554 (incorporated herein by reference), discloses the preparation of carboxylic acid amides by reacting an organic halide with a primary or secondary amine with carbon monoxide, in the presence of a palladium catalyst and a tertiary amine. It is disclosed that the tertiary amine is necessary to make the catalyst catalytic under the reaction conditions, and that the tertiary amine further acts as an acid acceptor to tie up the halides formed during the reaction. The problem with this process is that it is very hard to recover the halogen values from the salt prepared from the tertiary amine and the halogen. Some suggested processes for recovering the halogen values involved attempting a thermal cleavage between the amine and the halide values. The problem with this approach is that in most cases the temperatures necessary to achieve the thermal cleavage result in significant decomposition of the amines, driving up the costs of such a recovery.

What is needed is a process for the carbonylation of organic halides, wherein the halogen values generated by the process can be recovered in an efficient and reasonably economic manner.

SUMMARY OF THE INVENTION

This invention is a process for the carbonylation of an organic halide to prepare a carbonyl-containing compound, and recovery of halogen values in a useful form which comprises (a) contacting an organic halide with carbon monoxide and an esterifying agent, a primary or secondary amine, or hydrogen gas in an inert organic solvent in the presence of a water-insoluble tertiary amine or a pyridine ring-containing compound, and a catalytic amount of a Group VIII metal catalyst, under conditions such that an organic ester, amide, or aldehyde is prepared and the halide generated in the process forms a salt with a tertiary amine or pyridine compound wherein the halide is bromine or iodine;

(b) separating the organic ester, amide or aldehyde from the reaction mixture which contains the tertiary amine or pyridine compound-halide salt;

(c) contacting the reaction mixture containing the tertiary amine or pyridine compound-halide salt mixture with a concentrated aqueous solution of an alkali metal base or alkaline earth metal base under conditions such that an aqueous solution of an alkali metal halide or an alkaline earth metal halide and reaction solution containing the tertiary amine or pyridine compound is prepared;

(d) separating the aqueous solution from the reaction mixture; and (e) contacting the aqueous solution containing the alkaline earth metal halide salt or alkali metal halide salt with chlorine under conditions such that an alkali metal chloride salt or alkaline earth metal chloride salt and elemental halide is prepared.

This process allows the preparation of the organic esters, amides or aldehydes while further allowing the recovery of the valuable halide values in a reasonably efficient and economic manner.

DETAILED DESCRIPTION OF INVENTION

The organic halides useful in this invention include any halogenated organic compound which will undergo carbonylation under carbonylation conditions. Among preferred organic halides are allylic halides, vinylic halides, benzyl halides, aryl halides and heterocyclic halides. Carbonyl-containing compound refers herein to the reaction product of an organic halide and carbon monoxide. Preferred carbonyl-containing products are organic aldehydes, organic esters and organic amides.

In that embodiment wherein the organic halide is carbonylated in the presence of an esterifying agent, the carbonyl-containing product is an organic ester.

Where an organic halide is carbonylated in the presence of a primary or secondary amine, the carbonyl-containing compound is an amide. Conditions useful for such a process are described in Heck, U.S. Pat. No. 4,128,554 (incorporated herein by reference).

Where an organic halide is carbonylated in the presence of hydrogen gas, the carbonyl-containing compound prepared is an organic aldehyde. Conditions for such a process are taught in Heck, U.S. Pat. No. 3,960,932 (incorporated herein by reference).

The preferred carbonyl compounds preferred are the organic esters. More preferred organic halides are the 2-halo-1-alkenes which prepare acrylate esters.

The 2-halo-1-alkenes useful in this invention can be represented by the following formula

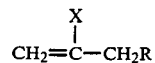

wherein X is bromine or iodine, and preferably bromine; wherein R is hydrogen, alkyl, cycloalkyl or aryl and may be substituted or unsubstituted. Preferably, R is lower alkyl or hydrogen. More preferably, R is hydrogen.

The 2-halo-1-alkenes can be esterified to prepare an acrylate ester. Acrylate esters represented by the formula below may be prepared by this process:

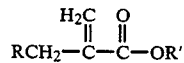

wherein
R is hydrogen, alkyl, cycloalkyl or aryl and may be substituted; and
R' is aryl, alkyl, cycloalkyl or benzyl and may be substituted.

The organic halide is carbonylated and esterified by contacting it with an esterifying agent and carbon monoxide, in the presence of a Group VIII metal catalyst and the water-insoluble tertiary amine to prepare the acrylate ester. The reaction wherein the organic halide is 2-halo-1-alkene and R'OH is the esterifying agent, can be represented by the following equation:

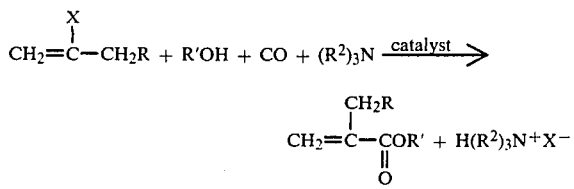

wherein R' is aryl, alkyl, cycloalkyl or benzyl and may be substituted with an alkyl, aryl, cycloalkyl, nitro, cyano, ester, carboxylate, amide, aldehyde, hydroxyl, amino, substituted amino or halogen, if these groups are less reactive than the other groups in the reactants which are intended to take part in the reaction; $R^2$ is alkyl or cycloalkyl of from 1 to 20 carbon atoms, wherein the total carbon atoms of all $R^2$'s is 14 or greater; and X and R are as previously defined.

The ester produced is separated from any unreacted materials, the catalyst, the halogen, acceptor and any solvent used, by any suitable process, such as distillation.

The esterifying agent (R'OH) used in the esterification of the organic halide may be any alcohol or phenol that has a reactive hydroxyl group. Alcohols and phenols with 1 to 20 carbon atoms or more may be employed. Examples of such alcohols and phenols include paraffinic alcohols and cycloparaffinic alcohols such as methanol, ethanol, propanol, phenol, cresol, xylenol, naphthol, cyclopentanol and cyclohexanol. Polyols, such as diols and triols may also be used, for example, ethylene glycol and glycerol.

The order of reactivity of alcohols from most to least is primary, secondary and tertiary. R' is preferably a $C_{1-10}$ lower alkyl and substituted or unsubstituted phenol, more preferably R' is a $C_{1-10}$ lower alkyl and most preferably R' is a methyl group.

Carbonates of the formula

R'OCOR' and (poly)glycol monoethers of the formula

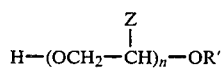

wherein R' is as defined above; n is an integer from 1 to 10; and Z can be, separately in each occurrence, hydrogen or methyl, can also be reacted with the 2-halo-1-alkene to prepare the α-acrylate esters. R' is preferably a $C_{1-10}$ lower alkyl and most preferably a methyl group.

A tertiary amine or a pyridine-containing compound is used to prevent the formation of free hydrogen halide or to reduce any hydrogen halide formed. The presence of a free hydrogen halide in the reaction can create problems because of its corrosive nature and inhibition of the reaction.

In this invention a tertiary amine or pyridine-containing compound is added to the reaction to function as a halogen acceptor. Tertiary amines and pyridine-containing compounds useful in this invention are those which are insoluble in water and capable of forming a salt with a halide value. Suitable amines are represented by the formula $(R^2)_3N$ wherein $R^2$ is separately in each occurrence, alkyl or, cycloalkyl of 1-20 carbon atoms with the proviso that the total number of carbon atoms in the $R^2$'s is greater than 14. Preferably, $R^2$ is a $C_{6-20}$ alkyl or $C_{6-20}$ cycloalkyl group. Examples of tertiary amines which can be used include trihexylamine, tricyclohexylamine, triheptylamine, trioctylamine, cyclohexyldiisoctylamine, cyclohexyl-4-heptyloctylamine, cyclohexyl-2-ethylhexyloctylamine, 2-ethylhexyl-4-heptyloctylamine, tri-2-ethylhexylamine, di-2-ethylhexylmethylamine, didecylethylamine, tridodecylamine, didodecylmethylamine, dodecyldiisopropylamine, dodecyldibutylamine, dodecyldiisobutylamine, dodecylisobutylmethylamine, diisopentadecylmethylamine, diisopentadecylethylamine and diisopentadecylisopropylamine. At least one mole of amine for each mole of hydrogen halide produced should be added to the reaction.

Preferred pyridine-containing compounds useful in this invention correspond to the formula

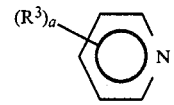

wherein $R^3$ is $C_{6-20}$ aryl, $C_{7-20}$ alkaryl, $C_{7-20}$ aralkyl or $C_{1-20}$ alkyl; and a is an integer of 0 to 5 inclusive. $R^3$ is preferably $C_{6-20}$ aryl, $C_{7-10}$ alkaryl, $C_{7-10}$ aralkyl or $C_{1-10}$ alkyl. $R^3$ is more preferably $C_{1-10}$ alkyl, phenyl, benzyl or methylphenyl. $R^3$ is most preferably $C_{1-4}$ alkyl. Preferably, a is 0 to 2 inclusive, and most preferably 0 or 1.

Carbon monoxide is added to the reaction by pressurizing the reaction vessel or zone with carbon monoxide gas and maintaining positive pressure with carbon monoxide gas throughout the process. Carbon monoxide can be present in an excess amount. Use of excess carbon monoxide can increase yields. It is desirable to employ from about 1.0 to about 25 or more moles of carbon monoxide per each mole of organic halide. A preferred amount is from about 1 to about 15 moles. The esterifying compound used to esterify the organic halide is preferably present in a molar ratio of the former to the latter of 1:1.

The catalyst is some form of Group VIII metal. Preferred Group VIII metals are palladium, cobalt, rhodium, iridium, nickel or platinum, with palladium most preferred. The metals can be employed either as homogeneous or heterogeneous catalysts. Homogeneous catalysts are preferred when the reaction is run in the liquid phase.

When the Group VIII metals are employed as heterogeneous catalysts, either the metal or a salt of the metal is supported on an inert carrier or activated carbon, silica alumina, silica gel, silicalite, activated clays, ion-exchange resins, or titanium, zirconium, magnesium, aluminum or silicon, or oxides thereof. Alumina supports are preferred.

These supported catalysts can be prepared by conventional means, well-known to the art. The palladium on support shows better catalytic activity where the catalyst is prepared from palladium chloride salt. Reduction temperatures between about 230° C. and 300° C. are preferred and give a more active catalyst.

Where palladium is used as the catalyst, between about 0.1 and 10 percent by weight of the support of palladium can be used, preferably between about 0.1 and 2.0 percent by weight of the support.

The reaction temperature is between about 150° C. and 300° C. for a heterogeneous catalyst, preferably between about 220° C. and 250° C. Pressure should be between about 100 and 5000 psi, preferably between about 400 and 1000 psi.

The Group VIII metal can also be used in a homogeneous catalyst. In this form the metal is used in a complex in which the metal can be reduced to the zero valence state, as it is believed that the catalytic species of these metals are the zero valent species. The complex can be represented by the formula $Y_mB(LR_3'')_p$ wherein B is a Group VIII metal; Y is chlorine, bromine, iodine, fluorine, acetate or $NO_3$ and the like; L is nitrogen, phosphorus or arsenic; m is an integer between 0 and 2; p is an integer between 0 and 4; and R" is separately in each occurrence, alkyl, aryl, alkoxy, aryloxy, thioalkyl, thioaryl or acetate.

L is preferably phosphorus; R is preferably alkyl, aryl or acetate; and B is preferably palladium, cobalt, rhodium, iridium, nickel or platinum and most preferably palladium. Both m and p are preferably 2.

These complexes may be prepared in situ, or prior to being added to the reaction. Whe palladium is used, between about 0.01 and 10 mole percent can be used, between about 0.1 and 1.0 mole percent is preferred.

The temperature for this reaction with a homogeneous catalyst is between about 50° C. and 200° C., preferably 100° C. and 160° C. Below 50° C., the reaction rate is too low, at 160° C. the catalyst begins to decompose.

The preferred method of carbonylation and esterification of a 2-bromo-1-alkene is a liquid phase reaction with a homogeneous catalyst.

The presence of oxygen can be detrimental to this reaction.

The carbonylation and esterification step may be run in the presence of a solvent. The solvent can be an excess of the alcohol, carbonate, (poly)-glycol, (poly)-glycol monoether or tertiary amines, which are present either to esterify the carbonylated organic halide, or present as a halogen acceptor. Alternatively, this step may be carried out in the presence of an inert solvent such as a hydrocarbon, ether or a (poly)glycol diether. The hydrocarbons employed can be either aliphatic, alicyclic or aromatic. Suitable solvents include cyclohexane, benzene, toluene, isooctane, xylene, mesitylene, diethylether, kerosene, diphenylene oxide, No. 9 oil, and (poly)alkylene glycol diethers. Of the above-described solvents those with a boiling point above 160° C. are preferred for use with a homogeneous catalyst as such catalysts decompose about 160° C. Ethylene glycol dimethyl ether is a preferred solvent for use with the homogeneous catalyst.

In one embodiment where the 2-halo-1-alkene is 2-bromopropene and the alcohol is methanol, the acrylate ester prepared is methyl methacrylate.

Upon completion of this carbonylation, the unreacted organic halide and the carbonyl-containing compound can be separated from the reaction mixture by conventional means. In one embodiment such separation can be performed by distilling off the organic halide, and carbonyl-containing compound from the reaction mixture.

Thereafter the reaction mixture can be contacted with an aqueous solution of a strong base under conditions such that an organic layer containing the free amine or pyridine-containing compound, and an aqueous layer containing the salt formed from the strong base and the halide value. The base can be any base which forms a halide salt when contacted in aqueous solution with the reaction mixture containing the amine halide salts formed during the previous step. In particular, preferred bases include alkali metal hydroxide, alkaline earth metal hydroxides, ammonium hydroxides, alkaline earth metal carbonates, alkali metal carbonates, and ammonium carbonates. Preferred bases are the alkali metal hydroxides, alkaline earth metal hydroxides, with the alkali metal hydroxides being even more preferred. The most preferred base is sodium hydroxide.

A sufficient amount of the aqueous solution of base is contacted with the reaction mixture so that a complete extraction of the desired amount of the halide values from the amine or pyridine-containing compound is achieved. Under preferred conditions a sufficient amount of the aqueous solution of base is used so that all of the halide values are removed from the organic reaction mixture. The concentration of the base in the aqueous solution is not critical. Such concentration should be as high as possible so as to reduce the volume of water necessary to perform this process. Preferably, concentrations of base in the water are 5 weight percent or greater, most preferably 20 weight percent or greater.

At the end of the contacting of the reaction mixture and the aqueous base, a two-phase system will result in which the organic reaction mixture phase will contain the free amine or pyridine-containing compound, and if the previous step was a homogeneous reaction, the homogeneous catalyst, which may then be recycled for further use in carbonylation, and an aqueous phase containing the salt of the halide value and the base from the aqueous solution. This aqueous phase is further processed to recover the halide value. The salt formed can be an alkali metal halide, alkaline earth metal halide, or ammonium halide. More preferably the salt is an alkali metal halide, and most preferably a sodium halide.

Upon completion of the contacting, said contacting taking place for a period sufficient for the desired amount of halide to be extracted from the organic reaction mixture, the organic phase and the aqueous phase are separated by conventional means known in the art. One preferred embodiment is by decantation of one phase away from the other phase.

The contacting of the organic reaction mixture with the aqueous base can take place at any temperature at which the formation of a salt from the base and the halide values takes place. Preferred temperatures are between about 20° C. and 100° C., with most preferred temperatures being between about 25° C. and about 50° C.

Thereafter, the aqueous solution containing the halide salt is contacted with chlorine to form elemental halide and the salt of an alkali metal chloride, alkaline earth metal chloride or ammonium chloride. The elemental halogen can thereafter be contacted with hydrogen gas at elevated temperatures to prepare hydrogen halide. This process is described in *Kirk-Othmer: Encyclopedia of Chemical Technology*, 3d Ed., Vol. 4, p. 245 (incorporated herein by reference). This hydrogen halide can be used to prepare the 2-halo-1-alkene useful in the preparation of the acrylate esters. The process for preparing the 2-halo-1-alkene is described in Klun et al., U.S. Pat. No. 4,480,121 (incorporated herein by reference).

SPECIFIC EMBODIMENT

The following examples are included herein for illustrative purposes only and do not limit the scope of the claims or the invention. Unless otherwise stated all parts and percentages are by weight.

EXAMPLE 1

Carbonylation of 2-Bromopropene

To a stirred high pressure reactor is added 87.63 g of tris-(2-ethylhexyl)amine, 1.30 g of di-(triphenylphosphine)palladium chloride, 29.70 g of methanol and 15.12 g of 2-bromopropene. The reactor is pressurized to 375 psig with carbon monoxide, heated to 125° C. and stirred for 4.5 hours. The results by analytical gas chromatography shows complete conversion of 2-bromopropene and 95 percent selectivity to methyl methacrylate.

EXAMPLE 2

Isolation of Methyl Methacrylate Methanol Azeotrope

The crude reaction mixture is vented to remove carbon monoxide and the methyl methacrylatemethanol azeotrope distilled out at about 65° C. The analysis of the azeotrope by analytical gas chromotography shows only methyl methacrylate and methanol. When the distillation pot contents are cooled a white/yellow solid formed in a thick yellow oil. Analysis of the yellow oil shows only the free tertiary amine.

EXAMPLE 3

Caustic Extraction of Tris(2-Ethylhexyl)amine Hydrogen Bromide

The yellow solid in thick yellow oil from Example 2 is stirred for 2 days with 25 ml of 5N NaOH in a 250-ml round-bottom flask to extract the hydrogen bromide from the amine. This is done in air. After 2 days the organic and aqueous layers are separated. The organic phase is rinsed with water and put back into the carbonylation reactor. The aqueous phase now contains mainly sodium bromide.

EXAMPLE 4

Carbonylation of 2-Bromopropene with Recycled Tris(2-Ethylhexyl)-amine and Catalyst To a stirred high pressure reactor is added 67.72 g of recovered tris(2-ethylhexyl)amine and catalyst from Example 3, 33.11 g of methanol and 15.05 g of 2-bromopropene. The reactor is pressurized to 375 psig with carbon monoxide, heated to 125° C. and stirred for 24 hours. The results show 54 percent conversion of 2-bromopropene with complete selectivity to methyl methacrylate.

EXAMPLE 5

Carbonylation of 2-Bromopropene, Triphenylphosphine with Recycled Tris(2-Ethylhexyl)amine and Catalyst To a stirred high pressure reactor is added 54.41 g of tris-(2-ethylhexyl)amine and catalyst which has been caustic extracted as described in Example 3 after a very inactive carbonylation reaction (27 percent 2-bromopropene conversion in 20 hours). To the reactor is added 1.5 g of triphenylphosphine, 44.66 g of methanol and 14.67 g of 2-bromopropene. The reactor is pressurized to 300 psig with carbon monoxide, heated to 125° C., and stirred for 3 hours. The results show 93 percent conversion of 2-bromopropene and complete selectivity to methyl methacrylate.

What is claimed is:

1. A process for the carbonylation of an organic halide to prepare a carbonyl-containing compound and recovery of halogen values in a useful form which comprises
    (a) contacting a organic halide with carbon monoxide and an esterifying agent, a primary or secondary amine or hydrogen gas in an inert organic solvent in the presence of a water-insoluble tertiary amine or pyridine ring-containing compound, and a catalytic amount of a Group VIII metal catalyst, under conditions such that an organic ester, amide or aldehyde is prepared and the halide generated in the process forms a salt with tertiary amine or pyridine ring-containing compound wherein the halide is bromine or iodine;
    (b) separating the organic ester, amide or aldehyde from the reaction mixture which contains the tertiary amine or pyridine ring-containing compound-halide salt;
    (c) contacting the reaction mixture containing the tertiary amine or pyridine ring-containing compound-halide salt mixture with a concentrated aqueous solution of an alkali metal base or alkaline earth metal base under conditions such that an aqueous solution of an alkali metal halide or an alkaline earth metal halide and reaction solution containing the tertiary amine or pyridine ring-containing compound is prepared;
    (d) separating the aqueous solution from the reaction mixture; and
    (e) contacting the aqueous solution containing the alkaline earth metal halide salt or alkali metal halide salt with chlorine under conditions such that an alkali metal chloride salt or alkaline earth metal chloride salt and elemental halide is prepared.

2. The process of claim 1 wherein the halide is bromine.

3. The process of claim 2 wherein the reaction mixture is contacted with an aqueous solution of an alkali metal hydroxide.

4. The process of claim 3 wherein the concentration of the aqueous solution of alkali metal hydroxide is 5 weight percent or greater.

5. The process of claim 4 wherein the tertiary amines correspond to the formula $(R^2)_3N$ wherein $R^2$ is alkyl or cycloalkyl of from 1 to 20 carbon atoms with the proviso that the total number of carbon atoms is about 14 or greater, and the pyridine-containing compounds correspond to the formula

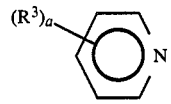

wherein $R^3$ is $C_{6-20}$ aryl, $C_{7-20}$ alkaryl, $C_{7-20}$ aralkyl or $C_{1-20}$ alkyl, and a is an integer of 0 to 5 inclusive.

6. The process of claim 5 wherein $R^2$ is $C_{6-20}$ alkyl or $C_{6-20}$ cycloalkyl, $R^3$ is $C_{6-10}$ aryl, $C_{7-10}$ aralkyl, $C_{7-10}$ alkaryl and $C_{1-10}$ alkyl.

7. The process of claim 6 wherein the reaction mixture and the aqueous solution of alkali metal hydroxide are contacted at a temperature of between about 20° C. and 100° C.

8. The process of claim 7 which further comprises
    (f) recovering the bromide from the aqueous solution of step e; and
    (g) contacting the bromine with hydrogen under conditions such that hydrogen bromide is formed.

* * * * *